(12) United States Patent
Novack

(10) Patent No.: US 10,137,230 B2
(45) Date of Patent: *Nov. 27, 2018

(54) SKIN INTERFACE DEVICE HAVING A SKIN ATTACHMENT DEVICE AND METHOD TO IMPLANT SAME

(71) Applicant: NuPulseCV, Inc., Raleigh, NC (US)

(72) Inventor: Brian Howard Novack, Santa Monica, CA (US)

(73) Assignee: NuPulseCV, Inc., Raleigh, NC (US)

( * ) Notice: Subject to any disclaimer, the term of this patent is extended or adjusted under 35 U.S.C. 154(b) by 463 days.

This patent is subject to a terminal disclaimer.

(21) Appl. No.: 14/659,375

(22) Filed: Mar. 16, 2015

(65) Prior Publication Data
US 2015/0258261 A1   Sep. 17, 2015

Related U.S. Application Data

(60) Provisional application No. 61/953,880, filed on Mar. 16, 2014.

(51) Int. Cl.
*A61M 1/10*  (2006.01)
*A61M 1/12*  (2006.01)

(52) U.S. Cl.
CPC ... *A61M 1/1008* (2014.02); *A61B 2560/0266* (2013.01); *A61B 2560/0276* (2013.01); *A61M 1/12* (2013.01); *A61M 2205/04* (2013.01)

(58) Field of Classification Search
CPC ............. A61M 39/04; A61M 39/0247; A61M 2039/0282; A61M 2039/025; A61M 2039/0264; A61M 1/1008; A61M 2205/04; A61M 2205/3592; A61M 2205/52; A61M 2205/70; A61M 2205/07; A61B 5/0472

USPC ........................................................ 600/509
See application file for complete search history.

(56) References Cited

U.S. PATENT DOCUMENTS

| | | | |
|---|---|---|---|
| 5,350,413 A | 9/1994 | Miller | |
| 5,904,646 A | 5/1999 | Jarvik | |
| 6,453,195 B1 | 9/2002 | Thompson | |
| 7,666,167 B2 | 2/2010 | Bierman | |
| 7,935,096 B2* | 5/2011 | Johansson | A61M 25/02 604/175 |
| 7,988,674 B2 | 8/2011 | Adams et al. | |
| 8,574,204 B2* | 11/2013 | Bourne | A61M 39/04 604/288.01 |
| 9,265,871 B2* | 2/2016 | Jeevanandam | A61M 1/106 |
| 2012/0108885 A1* | 5/2012 | Jeevanandam | A61M 1/1072 600/18 |
| 2013/0066365 A1* | 3/2013 | Belson | A61B 17/08 606/216 |

FOREIGN PATENT DOCUMENTS

DE   37 22 161 A1   1/1998

OTHER PUBLICATIONS

International Search Report dated Jun. 25, 2015 regarding PCT/US2015/020803.
Supplementary European Search Report dated Oct. 26, 2017, regarding EP 15765631.5.

\* cited by examiner

*Primary Examiner* — Catherine Voorhees
*Assistant Examiner* — Roland Dinga
(74) *Attorney, Agent, or Firm* — Perkins Coie LLP

(57) ABSTRACT

The present invention provides a skin attachment device for use with implantable medical devices which extend through the skin for prolonged durations.

57 Claims, 18 Drawing Sheets

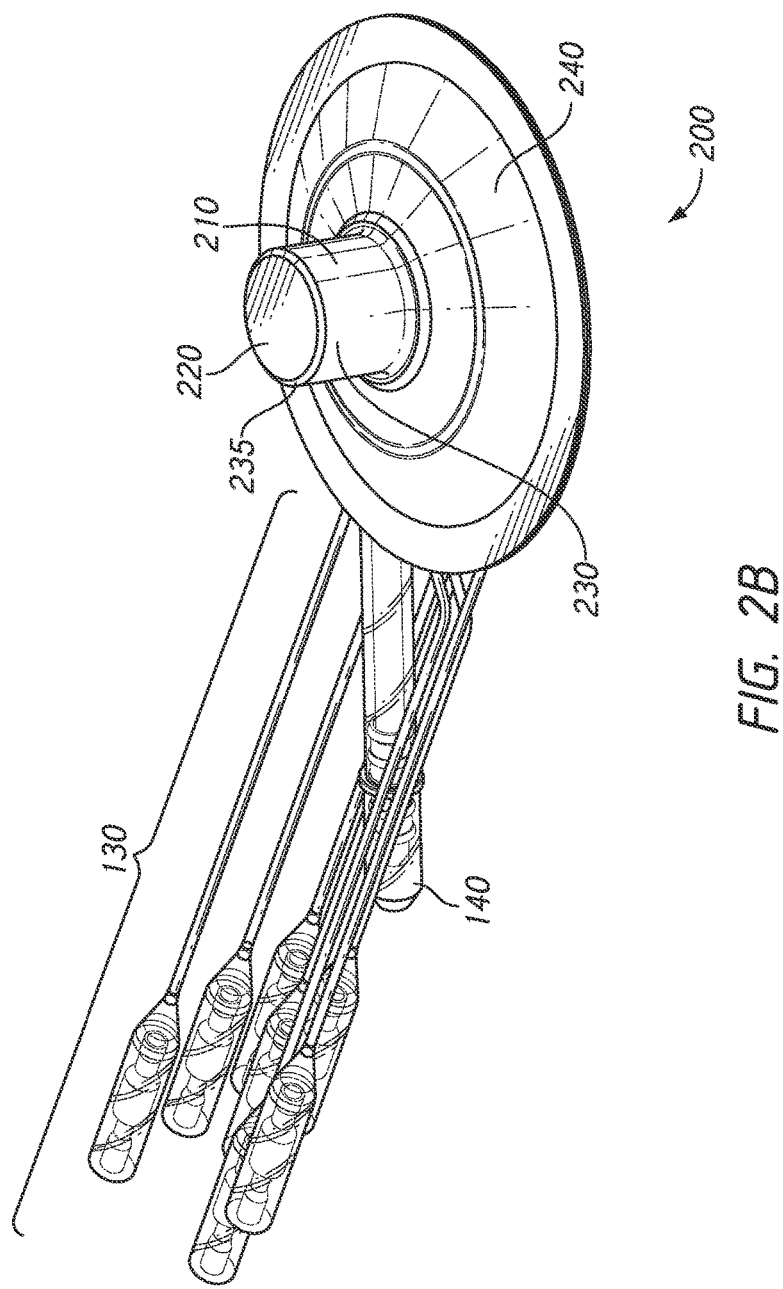

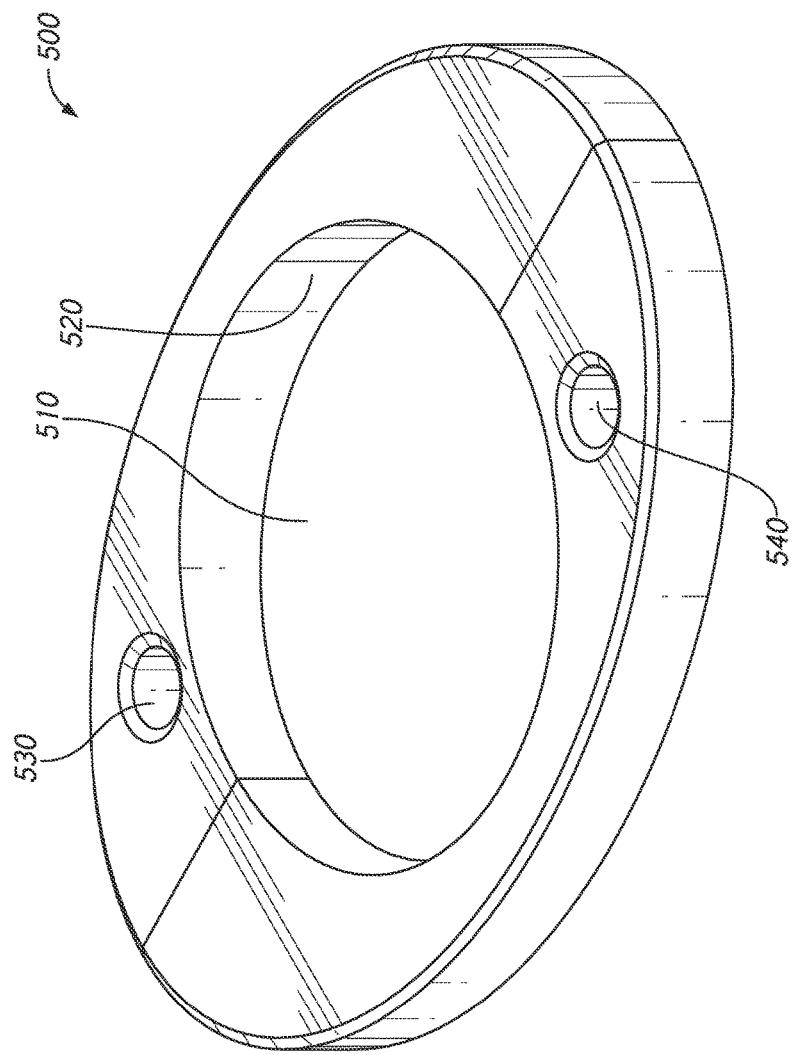

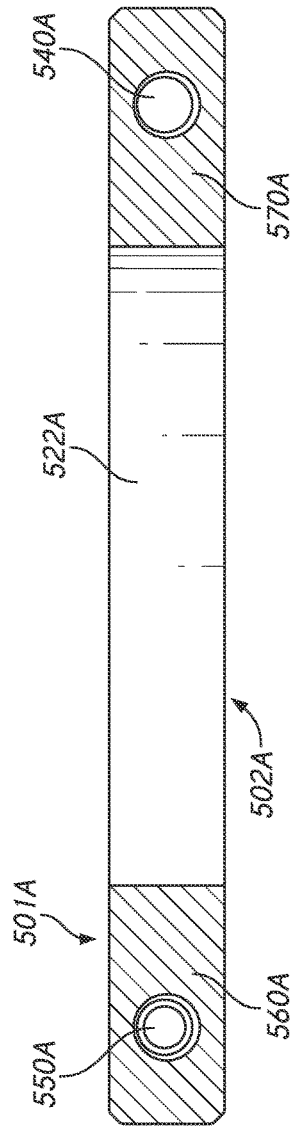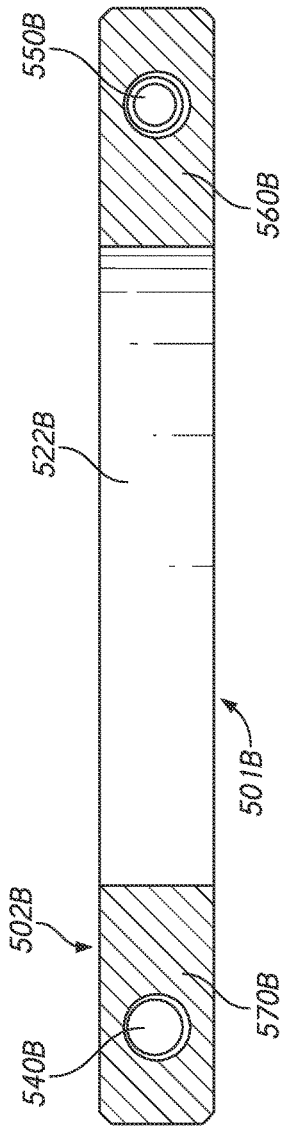
FIG. 5C
FIG. 5D

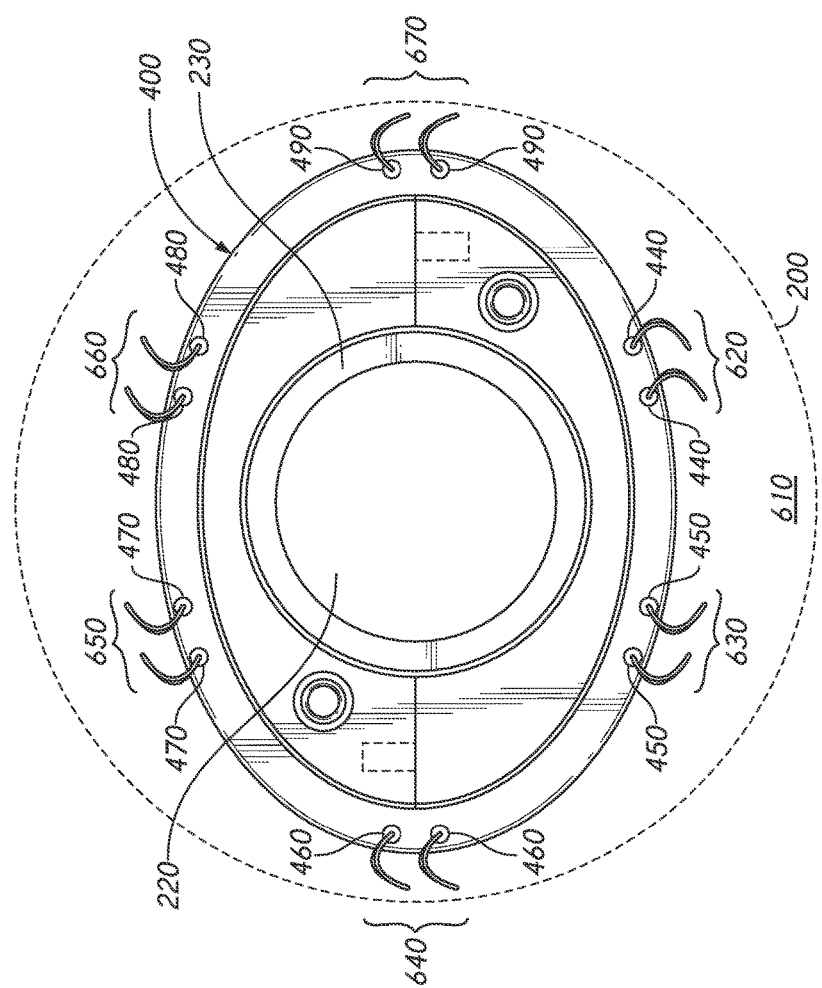

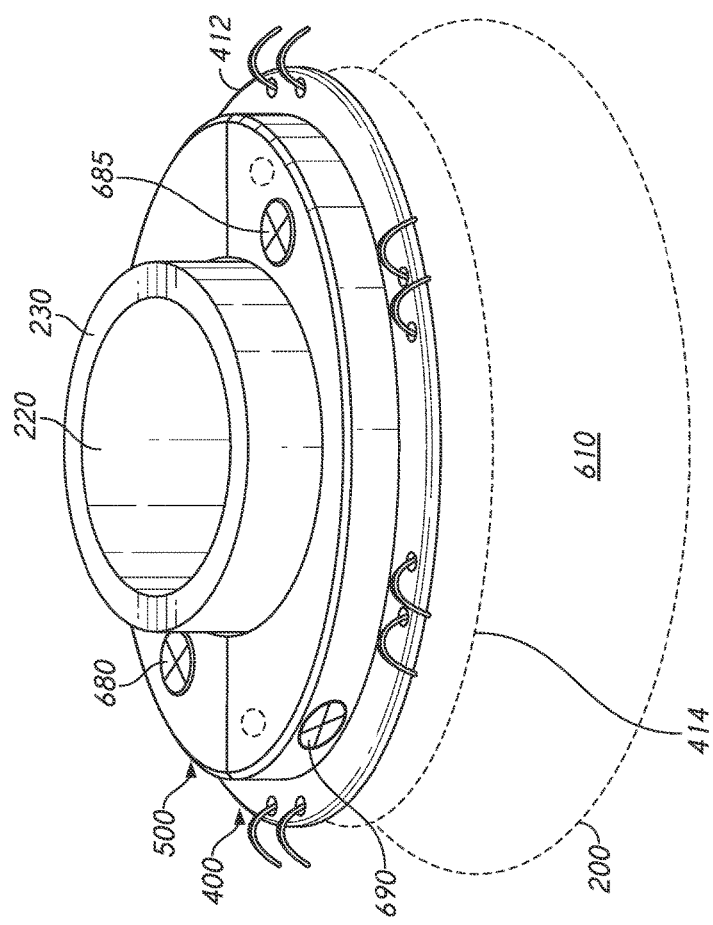

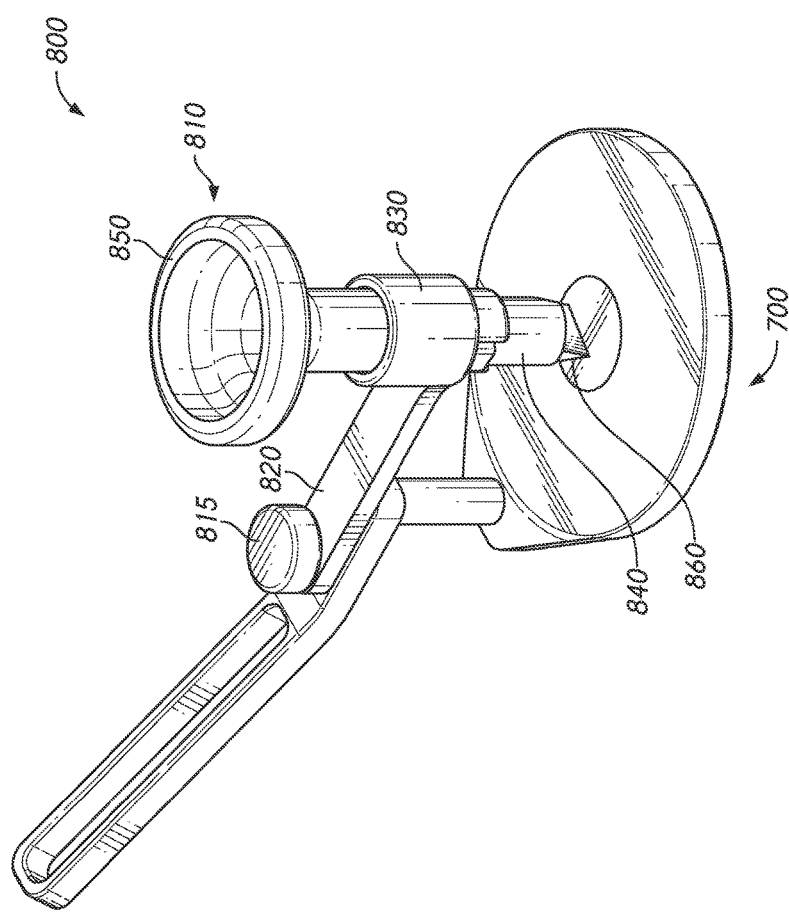

and is incor-

SKIN INTERFACE DEVICE HAVING A SKIN ATTACHMENT DEVICE AND METHOD TO IMPLANT SAME

CROSS REFERENCE TO RELATED APPLICATION(S)

This application claims the benefit under 35 USC § 119(e) to U.S. Application Ser. No. 61/953,880 filed Mar. 16, 2014, the disclosure of which is considered part of and is incorporated by reference in the disclosure of this application.

BACKGROUND OF THE INVENTION

Field of the Invention

The invention is directed to a skin interface device (SID), where the skin interface device includes a skin attachment device.

Background Information

Implantation of certain prior art skin interface devices required surgically forming a circular aperture in a patient's skin to allow a tubular portion of the skin interface device to extend outwardly from an implanted skin interface base portion.

The use of cardiac assist devices (CADs) is a well known method for treating heart failure and often utilize a SID. A pump is positioned inside the aorta, typically in the proximal descending aorta. The pump typically comprises a displacement volume of 40-50 cc, and works in series with the heart to augment blood flow. During diastole, the pump is inflated, thereby driving blood in the ascending aorta and aortic arch into the coronary arteries to supply oxygen to the heart muscle. During systole, as the left ventricle contracts, the pump is deflated so as to decrease the afterload.

The use of SIDs is well known. However, implantation of existing SIDs often lead to infection and other complications. There exists a need for a SID that may be used in multiple types of procedures without risk of infection.

BRIEF DESCRIPTION OF THE DRAWINGS

The invention will be better understood from a reading of the following detailed description taken in conjunction with the drawings in which like reference designators are used to designate like elements, and in which:

FIGS. 2A and 2B illustrate Applicants' SID base 200;

FIGS. 5A, 5B, 5C, and 5D, illustrate Applicants' fixturing assembly, and various sub-assemblies used to form same;

FIG. 6B is a top view showing Applicants' skin attachment device sutured to a patients' skin tissues during implantation of Applicants' SID;

FIG. 6C is a perspective view showing Applicants' fixturing device attached to a distal end of Applicants' implanted SID base, where that fixturing device is mechanically attached to Applicants' skin attachment device which has been sutured to a patient's skin tissues

FIG. 8A is a perspective view of Applicants' surgical guide instrument 800 used to subcutaneously implant Applicants' SID 400 within a patient;

DETAILED DESCRIPTION

Figure 1:
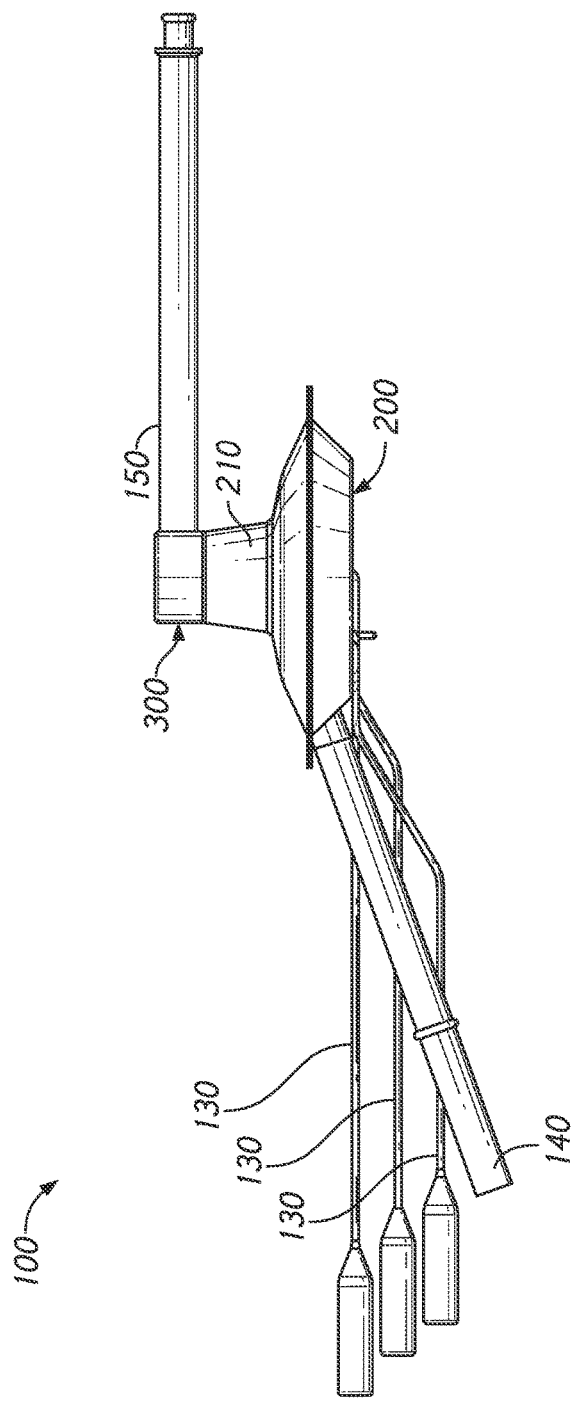
FIG. 1 illustrates Applicants' skin interface device ("SID") and various pneumatic conduits and sensor attachments thereto.

U.S. patent application having Ser. No. 14/017,109 and Ser. No. 14/476,656, and having a common inventive entity herewith, and assigned to the common assignee hereof, are incorporated herein in their entireties. The components, devices, modules, source code, and the like, disposed in the skin interface device ("SID") base and the SID cap described and claimed in the '109 and '656 applications are also disposed in the SID base and the SID cap described herein. In addition, as the functions and methods described and claimed in the '109 and '656 applications that utilize those components, devices, modules, source code, and the like, are also operative using the SID base and the SID cap described herein.

This invention is described in preferred embodiments in the following description with reference to the Figures, in which like numbers represent the same or similar elements. Reference throughout this specification to "one embodiment," "an embodiment," or similar language means that a particular feature, structure, or characteristic described in connection with the embodiment is included in at least one embodiment of the present invention. Thus, appearances of the phrases "in one embodiment," "in an embodiment," and similar language throughout this specification may, but do not necessarily, all refer to the same embodiment.

The described features, structures, or characteristics of the invention may be combined in any suitable manner in one or more embodiments. In the following description, numerous specific details are recited to provide a thorough understanding of embodiments of the invention. One skilled in the relevant art will recognize, however, that the invention may be practiced without one or more of the specific details, or with other methods, components, materials, and so forth. In other instances, well-known structures, materials, or operations are not shown or described in detail to avoid obscuring aspects of the invention.

While the skin attachment device of the present invention is generally discloses with use of a SID of the disclosure may be utilized with a variety of devices and in a variety of procedures which involve access though the skin in which infection may arise. For example, the present device may be utilized with devices and procedures utilizing Pic Lines, central IV access lines, LVAD drivelines, gastrostomy tubes, indwelling bladder catheters, orthopedic pins, and the like in which infection is a well documented problem.

The fundamental problem arises from the fact that no cellular in-growth occurs at the skin foreign body (metal, silicone) interface. The reason is the smooth surface does not allow it and just as importantly the constant movement breaks the adherence.

The present invention addresses both these issues. A linear incision is made to a minimal length such that the skin snaps into the elliptical rim of the SID. The concept of elliptical versus round is absolutely key. Round would require cutting out skin, while elliptical allows for a straight line incision with no skin excision. This makes closure of the defect much easier when the device is removed not to mention much more cosmetically acceptable. The rim itself creates a stable platform which is additionally secured by circumferential tie in sutures holes disposed in the lip of the skin attachment device. Further, vapor blasting of the titanium creates a surface where there is micro adherence akin to a cuticle on a nail bed. These features promote the long term interface necessary as a barrier against bacterial and fungal infection.

FIG. 1 shows Applicants' skin interface device ("SID") 100. A first end of a pneumatic drive line 150 is attached to SID 100, and a second end of drive line 150 is attached to a fluid driver which remains external to a patient's body. Pneumatic drive line 140 interconnects Applicants' SID 100 and an implanted cardiac assist device.

In certain embodiments, sensors are implanted into the patient, and these sensors connect to one or more communication interfaces 130.

Applicants' SID 100 comprises a SID base 200 (also interchangeably referred to herein as a skin attachment device) and a SID cap 300. SID base 200 and SID cap 300 can be coupled so as to create an air-tight conduit between the pneumatic drive line 140 and external air line 150, and such that the SID cap is rotatable around the SID base while maintaining an air-tight seal. In this way, pneumatic drive line 140, SID 100, and external air line 150, can be part of a closed fluid system. In certain embodiments, an air-tight seal is formed using gaskets and other sealing systems.

When implanted Applicants' skin interface device 100 includes a SID base 200, comprising a subcutaneous portion internal to the patient, in combination with a supracutaneous portion which is not disposed within the patient's body. SID cap 300 is attached to the supracutaneous portion of SID base 200. Those skilled in the art will appreciate that it is possible to implant SID 100 in a variety of different locations on the patient, for example abdominally or thoracically.

In certain embodiments, Applicants' SID base 200 further comprises a fabric cover disposed over a portion of the exterior surface thereof. In certain embodiments that fabric cover is formed to include a plurality of pores extending therethrough. In certain embodiments, the fabric cover comprises a polymeric material such as ePTFE of pore size 10-100 microns. In certain embodiments, the fabric cover is formed to include pores having a diameter of between about 30 to about 60 microns. The plurality of pores formed in the fabric cover comprise a diameter sufficient to allow cells to form attachments thereto.

Figure 2A:
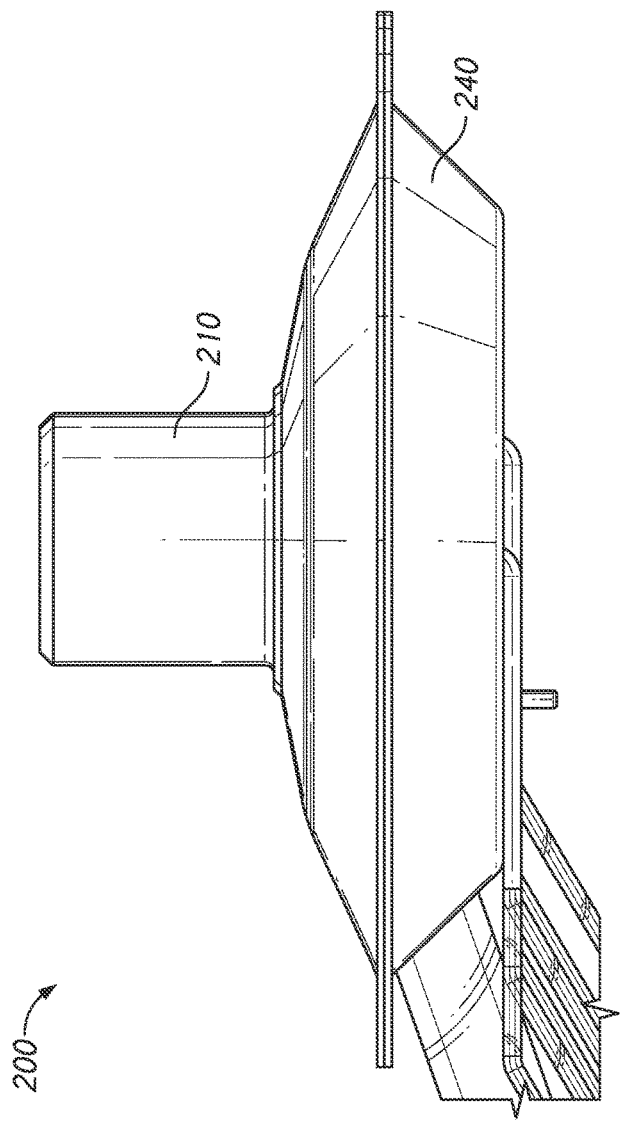

Referring to FIGS. 2A and 2B, SID base 200 comprises a disk-shaped portion 240 and a cylindrical assembly 210, wherein cylindrical assembly 210 extends outwardly from disk-shaped portion 240. The distal end 230 of cylindrical assembly 210 comprises an annular lip 235 which defines the opening of aperture 220.

Figure 3:
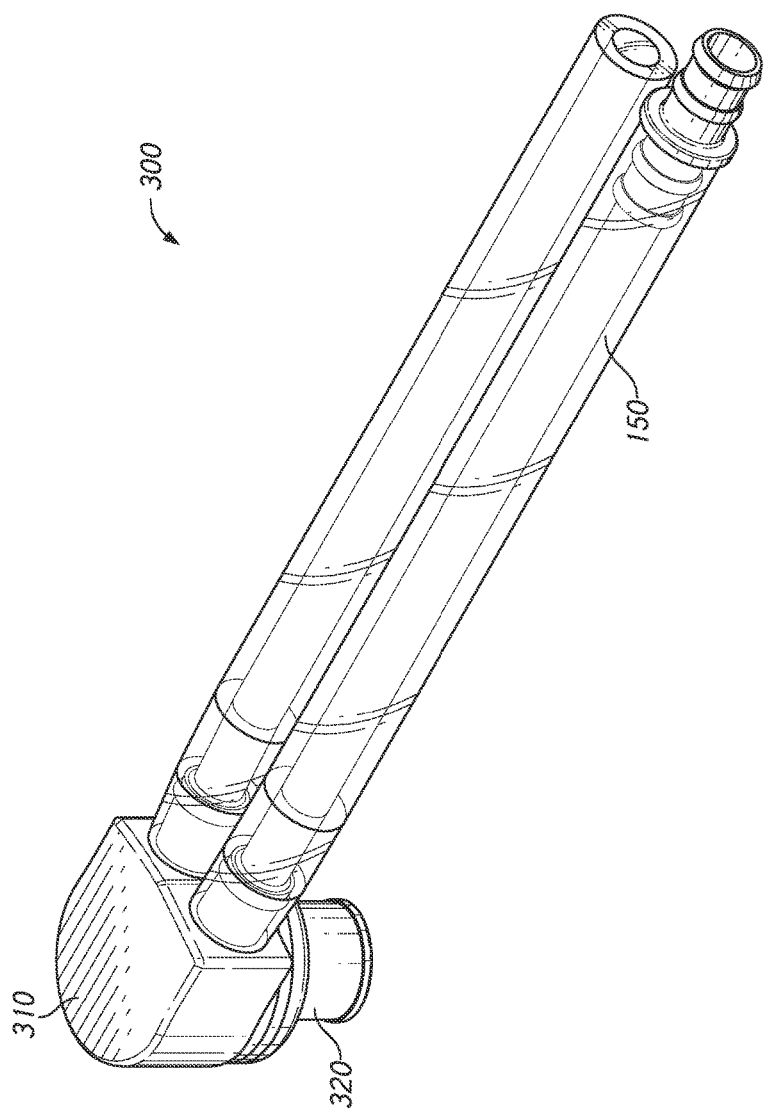
FIG. 3 illustrates Applicants' SID cap.

Referring to FIG. 3, SID cap 300 comprises a housing 310 having an electrical winding 320 extending therefrom. When SID 100 is assembled, electrical winding 320 is inserted into aperture 220 formed in cylindrical assembly 210.

Figure 6A:
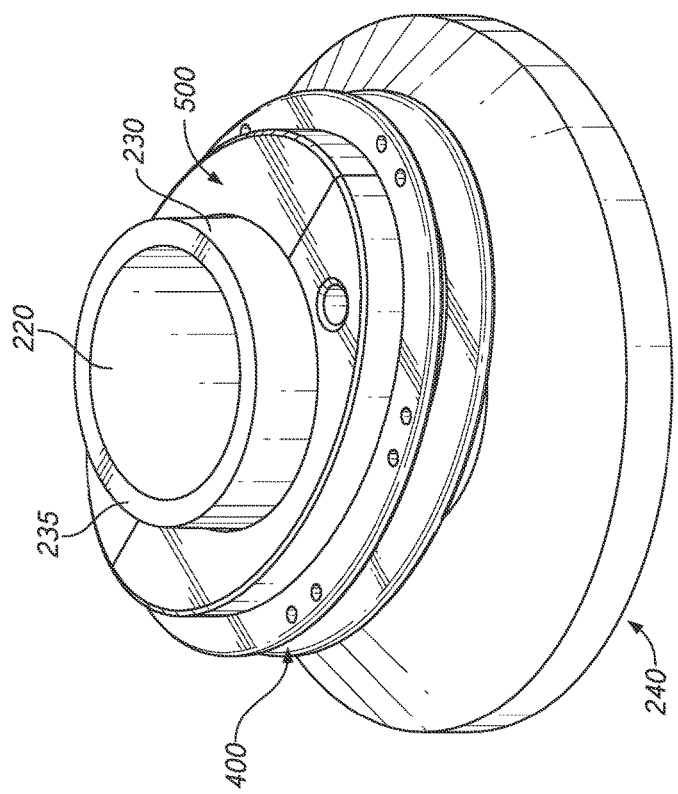
FIG. 6A illustrates a portion of Applicants' SID base and SID cap in combination with Applicants' skin attachment device and Applicants' fixturing assembly.

FIG. 6A illustrates a portion of disk-shaped SID base portion 240 and a portion of cylindrical assembly 210 wherein an elliptical-shaped skin attachment device 400 is disposed around a portion of cylindrical assembly 210, and wherein an elliptical-shaped fixturing assembly 500 is mechanically attached to the skin attachment device 400, and wherein that fixturing assembly 500 is also disposed around a portion of cylindrical assembly 210. The two "halves" of fixturing assembly 500 form a compression clamp on the neck of the SID Base. When assembled the clamps 501 and 503 are affixed to the neck 210 of the SID Base, and the skin attachment device 400 is affixed to the fixturing clamps thereby creating a rigid assembly.

As shown in FIG. 6A, the distal portion of cylindrical assembly 210, including annular lip 235, extend outwardly from both skin attachment device 400 and fixturing assembly 500. SID cap 300 can be inserted into aperture 220 when both skin attachment device 400 and fixturing assembly 500 are disposed around cylindrical assembly 210 as shown in FIG. 6A.

Figure 4A:
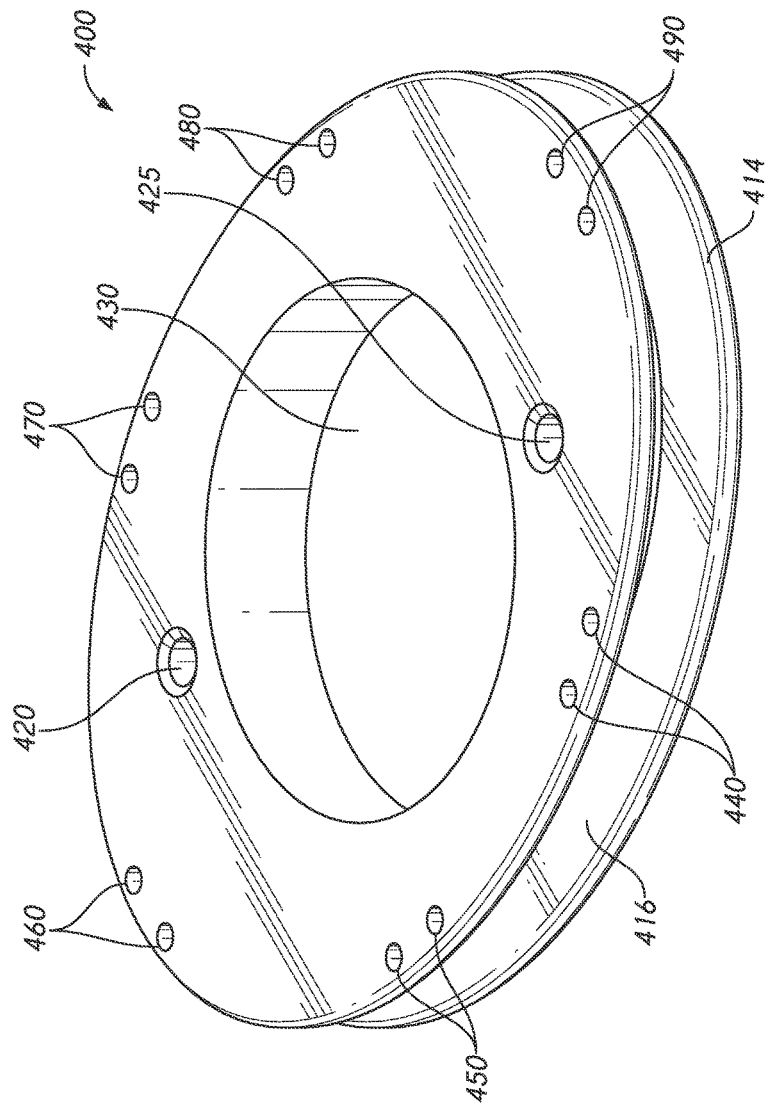
FIGS. 4A; 4B, and 4C, illustrate Applicants' skin attachment device.
Figure 4B:
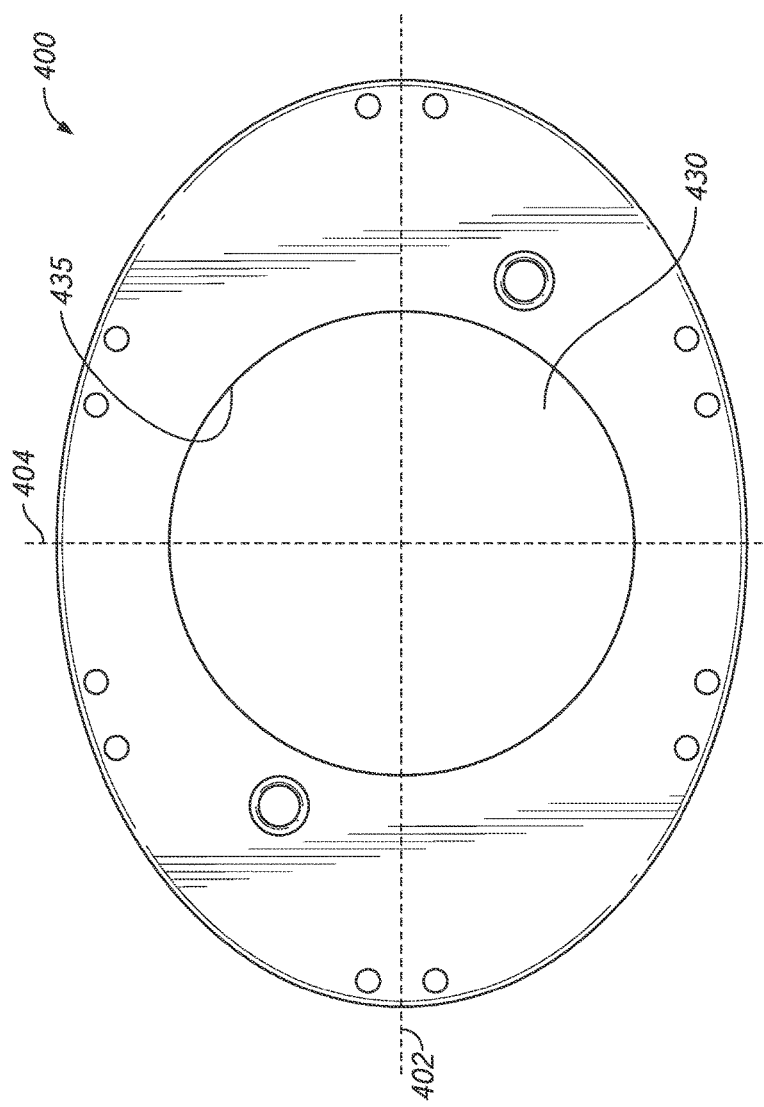
Figure 4C:
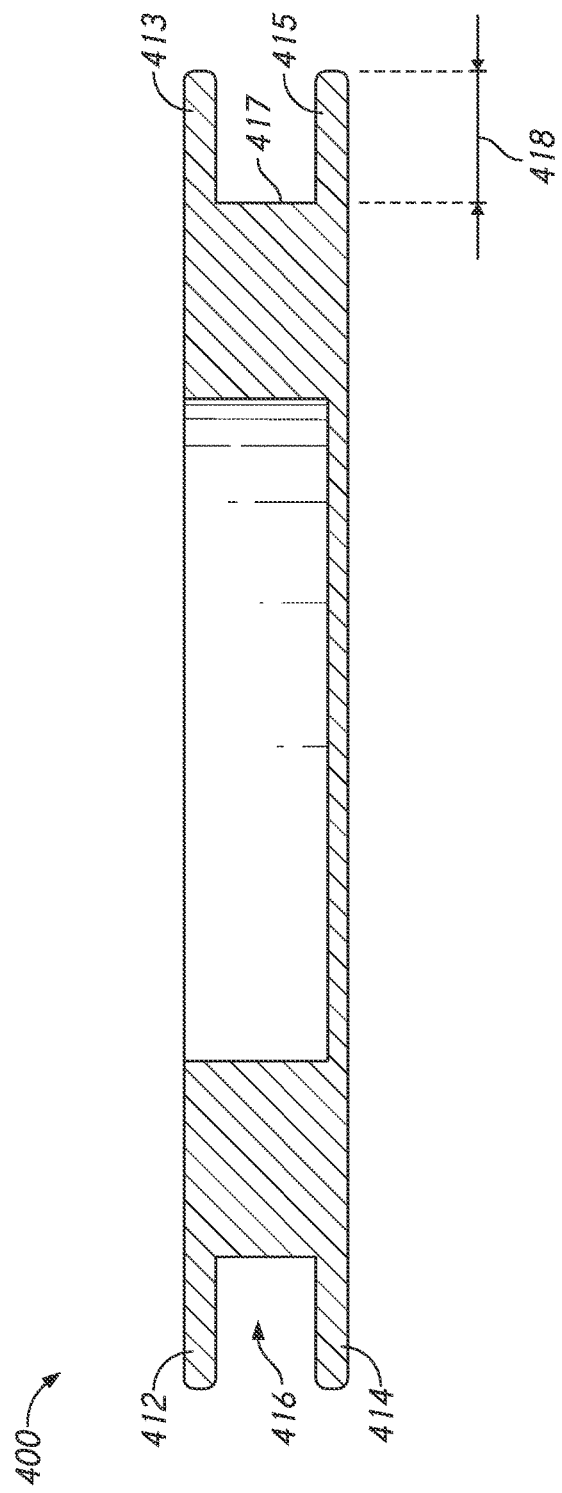

Referring now to FIGS. 4A, 4B, and 4C, skin attachment device 400 comprises an elliptical shape having a major axis 402 and a minor axis 404. Skin attachment device 400 comprises an upper lip 412 and a lower lip 414 which define an U-shaped pocket 416 formed along the periphery. In certain embodiments, U-shaped pocket 416 comprises a depth 418 of about 3 mm to about 4 mm.

U-shaped pocket 416 is defined by surfaces 413, 415, and 417. In certain embodiments, surfaces 413, 415, and 417, are textured with a surface roughness to facilitate adhesion of tissues thereto. The surgical procedure utilized to implant SID 100 into a patient, which is described in more detail hereinbelow, includes forming a linear incision at the implantation site, and then inserting skin attachment device into that incision such that tissues defining the periphery of the surgical incision are disposed within U-shaped pocket 416.

Skin attachment device 400 is formed to include a circular aperture 430 extending therethrough. Aperture 430 is defined by cylindrical wall 435. As described hereinabove, during implantation a distal portion of cylindrical assembly 210 will be passed through aperture 430 such that cylindrical wall 435 is in contact with cylindrical assembly 210.

Skin attachment device 400 is further formed to include six sets of aperture 440, 450, 460, 470, 480, and 490, extending through lip 412. During implantation, the tissues defining the periphery of a surgical incision described immediately hereinabove will be sutured to skin attachment device 400 using these 12 apertures.

Skin attachment device 400 is further formed to include a set of threaded apertures 420 and 425 extending into lip 412. During implantation, fixturing assembly 500 will be placed in contact with lip 412, such that a set of apertures 530 (FIG. 5A) and 540 (FIG. 5A) extending through fixturing device 500 overlie threaded apertures 420 and 425, respectively. Fastening devices can then to used to attach fixturing assembly 500 to skin attachment device 400.

Referring now to FIG. 5A, fixturing assembly 500 comprises an elliptical shape and is formed to include a circular aperture 510 extending therethrough. Aperture 510 is defined by cylindrical wall 520. In embodiments, surface 520 includes an annular groove disposed of the surface 520 to house a gasket ring. For example, an annular circular depression is provided on surface 520 to accept the gasket ring.

As described hereinabove, during implantation a distal portion of cylindrical assembly 210 will extend through aperture 430 in the sutured-in-place skin attachment device 400. Subsequently, fixturing assembly will be disposed about cylindrical assembly 210 such that cylindrical wall 520 is in contact with that cylindrical assembly 210.

Fixturing assembly 500 is formed to include vertical apertures 530 and 540 extending therethrough. As described hereinabove, during implantation fixturing assembly 500 will be placed in contact with tissue attachment device 400, such that vertical apertures 530 and 540 overlie threaded aperture 420 (FIGS. 4A, 4B) and 425 (FIGS. 4A, 4B), respectively. Fastening devices can then be passed through vertical apertures 530 and 540 and into threaded apertures 420 and 425, respectively, to attach fixturing assembly 500 to skin attachment device 400.

Figure 5B:
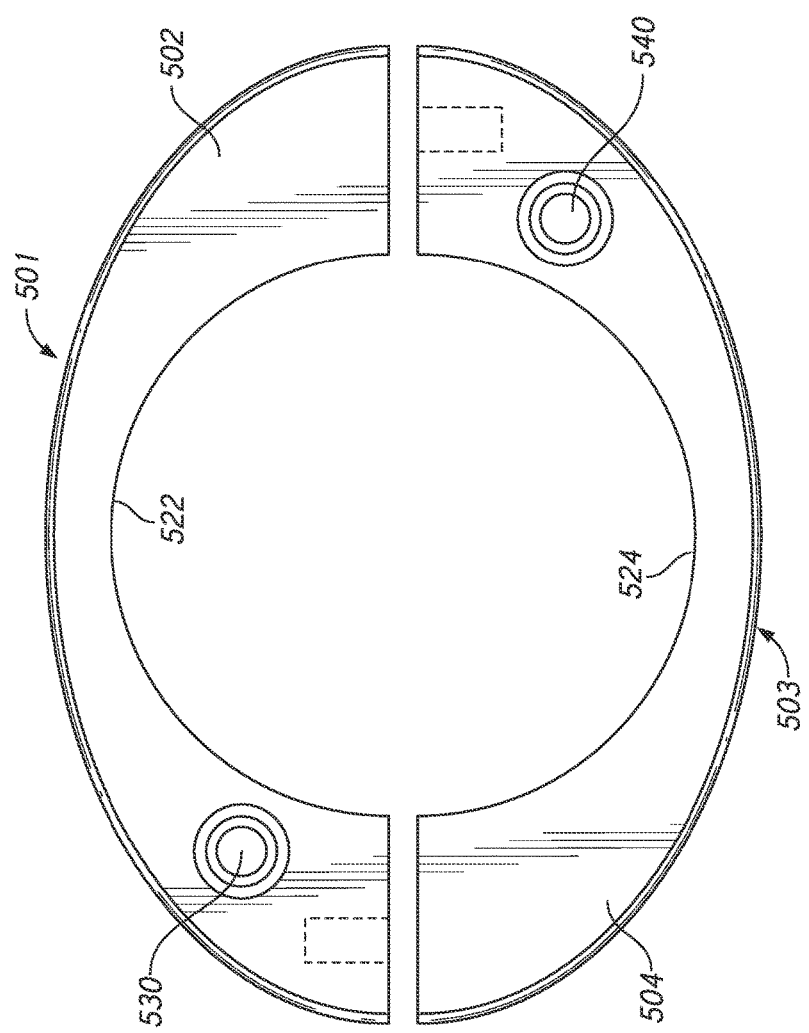

Referring to FIG. 5B, in certain embodiments fixturing assembly 500 comprises two sub-assemblies, namely sub-assemblies 501 and 503. Sub-assembly 501 comprises arcuate member 502 comprising curved surface 522. Sub-assembly 501 is formed to include aperture 530 extending therethrough. Sub-assembly 503 comprises arcuate member 504 comprising curved surface 524. Sub-assembly 503 is formed to include aperture 540 extending therethrough.

Referring now to FIGS. 5C and 5D, in certain embodiments the two sub-assemblies used to form fixturing assembly 500 are identical. In the illustrated embodiment of FIGS. 5C and 5D, fixturing assembly 500 is formed using a first sub-assembly 501A and a second sub-assembly 50IB.

Subassemblies 501A and 501B are both formed to include a threaded aperture 550A and 550B, respectively, extending inwardly into ends 560A and 560B, respectively, and lateral apertures 540A and 540B, respectively, extending through ends 570A and 570B, respectively. A first fastening device can be inserted through lateral aperture 560A and into threaded aperture 550B, and a second fastening device can be inserted through lateral aperture 560B and into threaded aperture 550A, to form fixturing assembly 500. Curved surface 522A in combination with curved surface 522B forms aperture 510.

In embodiments, the Applicants' skin interface device ("SID") 100 allows the design of the system to be composed of parts both implanted and external to the patient's body.

In certain embodiments, one or more sensors transmit data, by wire or wirelessly, to Applicants' SID 100. Examples of sensors include, without limitation, electrical leads to measure an electrocardiogram, sensors to detect body temperature, sensors to detect blood analytes (such as blood gases), sensors to detect intra-arterial pressure directly or indirectly, and/or sensors to measure humidity within an external pump. Indirect sensors include, for example and without limitation, a microphone to monitor heart sounds.

In certain embodiments, a controller is disposed in SID 100. In certain embodiments, a controller integral with an external driver.

In certain embodiments, signals from one or more sensors are used by the controller to monitor the cardiac cycle and, thereby, the counterpulsation cycle. In certain embodiments, combinations of signals from one or more sensors are used by the controller to monitor the cardiac cycle.

In certain embodiments, sensors are used to determine the state of the air inside the system. In certain embodiments, air pressure is measured to determine whether the pump is properly inflating, or if there is a leak in the system. In certain embodiments, data from the air pressure sensor is communicated to the controller.

In certain embodiments, sensors for arterial blood pressure are in communication with controller. In certain embodiments, these sensors communicate a detected arterial blood pressure to the controller, either by wire or wirelessly.

Applicants' SID 100 comprises a SID base 200 and a SID cap 300. SID base 200 and SID cap 300 are coupled so as to create an air-tight conduit between the pneumatic drive line 140 and external air line 150. In this way, pneumatic drive line 140, SID 100, and external air line 150, can be part of a closed fluid system. In certain embodiments, an air-tight seal is formed using gaskets and other sealing systems.

When implanted Applicants' skin interface device 100 includes a SID base 200, comprising a subcutaneous portion internal to the patient, in combination a supracutaneous portion. SID cap 300 is attached to the supracutaneous portion of SID base 200. Those skilled in the art will appreciate that it is possible to implant SID 100 in a variety of different locations on the patient, for example abdominally or thoracically.

Referring now to FIGS. 4A and 4C, Applicants' SID 100 wirelessly provides electrical energy from SID cap 300 to SID base 200, and also wirelessly and bi-directionally passes electrical signals, i.e. data, between SID cap 300 and SID base 200. In order to optimize the transmission of power from SID cap 300 to SID base 200, and at the same time optimize the transmission of data between SID cap 300 and SID base 200, Applicants have "decoupled" the transmission of power from the transmission of data. The transmission of power from SID cap 300 to SID base 200 is done by induction.

Applicants' SID 100 includes a transformer comprising a primary winding disposed in SID cap 300 and a secondary winding disposed in SID base 200. The SID transformer is configured to power Applicants' SID 400 via an external power source, such as a battery, or conventional 120V or 220V alternating current. During operation of the device the SID transformer transfers power from the external power source to the patient. Importantly, however, the patient is not directly wired to the external power source and is therefore not directly connected to the external power source. SID cap 300 comprises an annular sleeve attached to and extending outwardly from a housing. The annular sleeve defines an interior bore having a diameter. The primary winding is disposed around the exterior surface of the annular sleeve.

A cylindrical member may be disposed within a bore formed in a tubular portion. The secondary winding is disposed around the cylindrical member. In certain embodiments, connectors may be used to attach EKG sensors to Applicants' SID 100. In certain embodiments, connectors may be used to attach sensor leads from an implants pressure sensor to Applicants' SID 100.

SID cap 300 is configured to be disposed over, and rotationally attached to the tubular portion of SID base 300, to form a wireless power transfer assembly. After such attachment, the relative positions of the primary winding and the secondary winding are fixed both laterally and vertically. A rotation of SID cap 300 about SID base 200 cannot alter the electrical/magnetic coupling of the primary winding and the secondary winding.

In embodiments, SID cap 300 and the tubular portion of SID base 200 are fixed to one another so that they remain attached to each other but are rotatable with respect to one another once initially connected to one another. In this way, SID base 200 can remain stationary with respect to the patient while SID cap 300 can be rotated to accommodate any convenient orientation of the external drive line 140 and any external electrical line. Such rotational decoupling can help reduce or prevent tugging or other stress on the patient's skin or other organs.

In certain embodiments, the primary winding comprises Np turns and the secondary winding comprises Ns turns. In certain embodiments, Np is substantially equal to Ns. In these embodiments, when first electrical power having a voltage Vp is passed through the primary winding, a second electrical power having a voltage Vs is induced in the secondary winding, wherein Vp substantially equals Vs. By "substantially equals," Applicants mean within about plus or minus ten percent (10%).

In certain embodiments, Np is less than Ns. In these embodiments, the wireless power transfer assembly comprises a "step up" transformer wherein Vs is greater than Vp. In certain embodiments, Np is greater than Ns. In these embodiments, the wireless power transfer assembly comprises a "step down" transformer wherein Vs is less than Vp.

In certain embodiments, annular sleeve 602 is formed from a material comprising a relative magnetic permeability greater than 1. In certain embodiments, the annular sleeve is formed from a ferrite. As those skilled in the art will appreciate, ferrites are ceramic materials with iron (III) oxide ($Fe_2O_3$) as a principal component. In certain embodiments, annular sleeve is formed from one or more "soft ferrites." In certain embodiments, annular sleeve comprises nickel, zinc, and/or manganese moieties. In these embodiments, the annular sleeve comprises a low coercivity and the annular sleeve's magnetization can easily reverse direction without dissipating much energy (hysteresis losses), while the material's high resistivity prevents eddy currents in the core.

Those skilled in the art will appreciate, that the size of a transformer decreases as the frequency of power passed through the primary winding increases. Use of a soft ferrite facilitates the use of higher frequencies.

In certain embodiments Applicants' SID 100 utilizes a wireless power transfer assembly comprising a polyetheretherketone ("PEEK") core. In certain embodiments Applicants' SID 100 utilizes a wireless power transfer assembly comprising a polyetherimide core.

In certain embodiments, the use of a soft ferrite moieties and frequencies between about 100 kHz and about 1 MHz, in combination with the invariant vertical and lateral alignment of the primary winding and the secondary winding, maximizes the efficiency of wireless power transmission within SID 100.

Power that is not effectively transmitted from the SID cap 300 to the SID base 200 is lost as heat. SID 100 is an implantable device and is intended for long-term use in a patient. It is known that at temperatures in the range of about 41° C. to about 43° C., damage to adjacent tissues can begin. It is further known that at temperatures greater than about 43° C., surrounding tissues will be damaged.

Needless to say, tissue damage in near vicinity to an implanted medical device can be a source of infection. The optimized efficiency of power transmission within Applicants' implantable SID 100 allows the use of more power within that device without increasing a likelihood of infection.

Applicants' SID 100 further comprises a pair of infrared transceiver assemblies to bi-directionally wirelessly transmit data between SID cap 300 and SID base 200. SID cap 300 comprises a first infrared data transceiver assembly. SID base 200 comprises a second infrared transceiver assembly.

In certain embodiments, the infrared transceiver assemblies each comprise at least one infrared diode and signal processing circuitry. In certain embodiments, the infrared transceiver assemblies each utilize one or more infrared diodes emitting infrared energy at wavelengths between about 780 nm to about 1550 nm.

In certain embodiments, the infrared diode and processing circuitry are efficient enough to fit into a small module whose transceiver has the dimensions of a child's fingernail. In certain embodiments, the infrared transceiver assemblies, are capable of exchanging data at a rate of about 1 Gbps.

The infrared transceiver assembly disposed in SID base 200 comprises one or more infrared diodes. The infrared transceiver assembly disposed in SID cap 300 comprises one or more infrared diodes.

In certain embodiments Applicants' SID 100 comprises a controller. The controller comprises a processor and non-transitory computer readable medium. In certain embodiments, the computer readable medium comprises a non-volatile memory device, such as and without limitation battery-backed up RAM; an electronic storage medium; a hard disk drive assembly comprising a magnetic disk storage medium and ancillary hardware, software, and firmware needed to write data to, and read data from, the magnetic disk; an optical disk drive assembly comprising a rewriteable optical disk and ancillary hardware, software, and firmware needed to write data to, and read data from, the optical disk.

In certain embodiments, the computer readable medium comprises a rewritable memory device, such as and without limitation an EEPROM or NAND flash memory.

In certain embodiments, patient data is encoded in the computer readable medium. In certain embodiments, patient data comprises timing data related to the inflation and deflation of an external pump. When a patient changes drive units, the new drive unit reads the timing data from Applicants' SID 100 and adjusts its timing parameters accordingly.

In certain embodiments, the computer readable medium is configured to store data; e.g., in primary or secondary memory storage module, accumulated during operation of Applicants' SID 100, or information obtained during a doctor's visit. The information may be accessed either by a doctor, for example to investigate the past performance of Applicants' SID 100, or to obtain data on the patient's health as detected by sensors used to collect data during operation. Or the information may be accessed by a processor, for example to set parameters for operation of Applicants' SID 100.

In certain embodiments, the computer readable medium is configured to store various types of data accumulated during operation of Applicants' SID 100. For example, data obtained from sensors by be stored in a memory storage module to assess a patients well being, such as EKG signals, pulse, body temperature, blood pressure, blood analytes and the like, all which may be measured and stored as a function of time. Additionally, data may be stored to assess performance of Applicants' SID 100 during operation. For example data pertaining to operational parameters of components of Applicants' SID 100 may be stored, such as drive unit usage, including timing and volume of pumping, as well as errors in component operation or function. In this manner component usage logs may be compiled and stored on the computer readable medium. Similarly, event logs may be compiled and stored on the computer readable medium. As discussed above, the information may be accessed either by a doctor, for example to investigate the past performance of Applicants' SID 100 or to obtain data on the patient's health. Or the information may be accessed by the processor, for example to set parameters for operation of Applicants' SID 100.

Computer readable program code is encoded in the computer readable medium. The processor is in bi-directional communication with the computer readable medium. The processor utilizes computer readable program code to operate Applicants' SID 100.

In certain embodiments, the processor, the computer readable medium, and the computer readable program code, are integrated in an Application Specific Integrated Circuit.

In certain embodiments the housing for base 200 is machined from a block of titanium. The housing is formed to include a central tubular portion.

In embodiments, Applicants' SID is provided with circuitry that allows the device to withstanding an externally applied electrical shock from a conventional defibrillation device (about 5000V) while still being able to detect, process and store low power signals, such as those from an EKG sensor. The SID includes passive circuitry which functions to "clamp" down a high voltage shock which is administered to a patient who is wearing the device but required defibrillation. This feature ensures that the device is not rendered nonoperational which could pose great harm to the patient. Advantageously, however, patients undergoing cardiac support through use of the device according to the invention can be expected to continue functioning at no lower than baseline (cardiac function prior to device operation) and potentially at a higher level of function, without risk of advsere cardiac effects (see, e.g., Kantrowitz, et al., *ASAIO Journal*, 41 (3): M340-M345 (1995) (no histological damage following in vivo operation and deactivation of a ventricle assist device in cows); Li, et al., *ASAIO Journal*, 46(2): 205 (2000) (no ill effects from deactivation then reactivation after two months); and, Jeevanandam, et al., *Circulation*, 106:1-183-1-188 (2002) (cardiac evaluation in humans implanted with a permanent ventricle assist device)).

SID cap 300 may additionally include one or more access ports for both electrical signals and fluid lines (not shown). For example, SID cap 300 may have additional access ports for fluid communication with more than one external drive line, such as multiple drive lines. Similarly, SID cap 300 may include one or more access ports for external electrical lines. For example, one or more access ports may be provided such that the SID may be connected to external electrical line for connection to an external processor or memory. In this manner data may be transferred from the computer readable medium to an external processor. The access port may also be configured to receive data from an external processor.

Power supplied to the SID cap is provided to the primary winding, which wirelessly provides power to SID base 200 via the secondary winding. In certain embodiments, the controller receives power from the secondary winding. In certain embodiments, SID base 200 comprises one or more rechargeable batteries, wherein those one or more rechargeable batteries receive power from the secondary winding.

In certain embodiments, SID cap 300 further comprises one or more communication ports. In certain embodiments, the communication ports may include a USB port.

In certain embodiments, the communication port comprises an IEEE 1394 interface, i.e. a "firewire" port. In certain embodiments, the communication port is in communication with the controller via infrared transceivers.

In certain embodiments, SID cap 300 further comprises a wireless communication module configured to communicate wirelessly with one or more computing devices external to SID 400. In certain embodiments, the wireless communication module is in communication with the controller via infrared transceivers.

In certain embodiments, wireless communication module 630 utilizes "WI FI" technology in accord with the IEEE 802.11 Standard. As those skilled in the art will appreciate, the 802.11 family consist of a series of half-duplex over-the-air modulation techniques that use the same basic protocol. Standard 802.11n is a new multi-streaming modulation technique. Other standards in the family (c-f, h, j) are service amendments and extensions or corrections to the previous specifications.

In certain embodiments, the wireless communication module utilizes "Bluetooth" technology. As those skilled in the art will appreciate, Bluetooth is a wireless technology standard for exchanging data over short distances (using short-wavelength radio transmissions in the ISM band from 2400-2480 MHz) from fixed and mobile devices, creating personal area networks (PANs) with high levels of security.

In certain embodiments, the controller can provide data to one or more computing devices external to Applicants' SID. In certain embodiments, controller utilizes a wireless communication module. In certain embodiments, the controller utilizes a wired interconnection with the one or more external computing devices utilizing the communication port.

Figure 7:
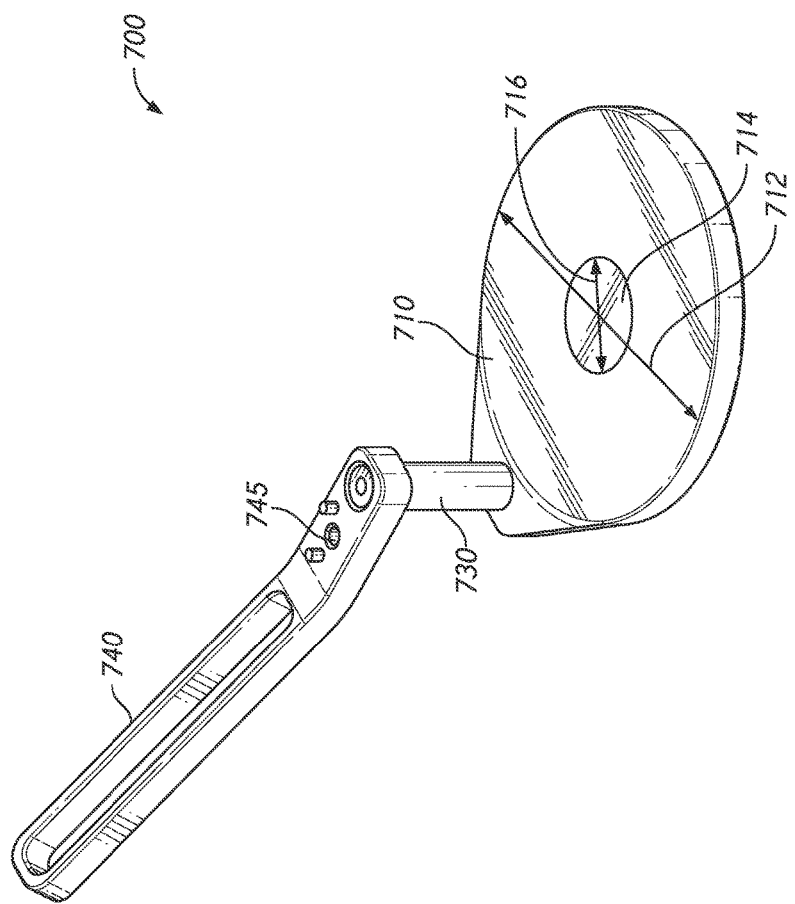
FIG. 7 is a perspective view of a handle and base portion 700 of Applicants' surgical guide instrument 800 used to subcutaneously position Applicants' SID 400 within a patient.

Referring now to FIGS. 7 and 8A, Applicants' SID 100 can be implanted into a patient using Applicants' surgical guide instrument 800. Surgical guide instrument 800 comprises base portion 700 in combination with removeably attachable assembly 810.

Referring now to FIGS. 7 and 8A, Applicants' SID 100 can be implanted into a patient using Applicants' surgical guide instrument 800. Surgical guide instrument 800 comprises base portion 700 in combination with removeably attachable assembly 810.

Implantation of SID 100 and addition of skin attachment device 400 and fixturing assembly 500 to that implanted SID 100 requires use of a surgical guide instrument 800. Referring to FIG. 7, surgical guide instrument base portion 700 comprises platen 710 having a diameter 712. Platen 710 is formed to include plastic disk 714 having a diameter 716 disposed in the center of platen 710.

Implantation of SID 100 and addition of skin attachment device 400 and fixturing assembly 500 to that implanted SID 100 requires use of a surgical guide instrument 800 (FIG. 8A). Referring to FIG. 7, surgical guide instrument base portion 700 comprises platen 710 having a diameter 712. Platen 710 is formed to include plastic disk 714 having a diameter 716 disposed in the center of platen 710.

A first end of member 730 is attached to the periphery of platen 710 and extends upwardly therefrom. Handle 740 is attached to a second end of member 730. Handle 740 is formed to include a threaded aperture 745 extending inwardly therein from a top surface.

When preparing to subcutaneously implant Applicants' SID 100, a surgeon can subcutaneously insert platen 710 through a first lateral incision in the skin. The surgeon then utilizes platen 710 as a guide to dissect a subcutaneous pocket correctly dimensioned to accept Applicants' SID 100.

The subcutaneous pocket must be dissected upon fascia rather than subcutaneous fat in the subdermis. As a result, the portion of the cylindrical assembly 210 skin surface extending outwardly from the skin surface may vary by patient. The notched and gasketed subassembly 210 when "married" to subassembly 500, which is fixed to subassembly 400 allows for waterproof fixation of the SID base to the skin interface device 400 at various heights depending on the thickness of the patient's subcutaneous tissue.

Figure 8B:
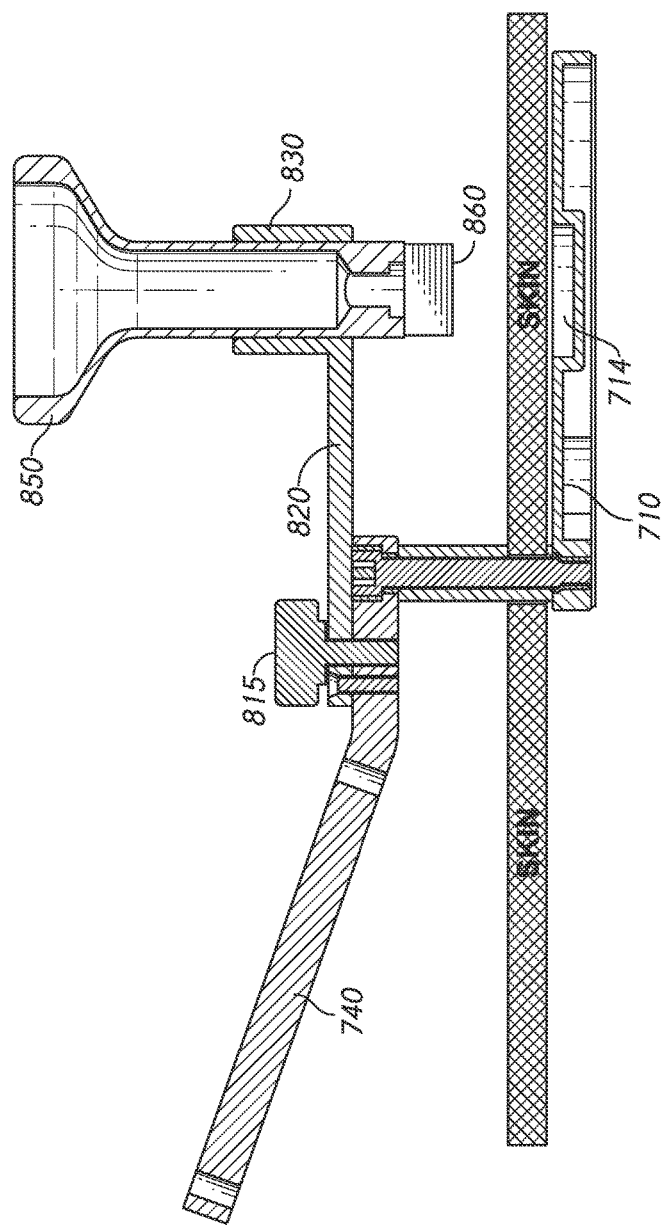
FIG. 8B is a section view of the surgical guide instrument 800, wherein bottom platen 710 has been used to form a subcutaneous pocket to receive Applicants' SID base 500, and wherein upper assembly 810 is being used to form a linear incision in the skin through which a tubular portion of SID base 500 can extend outwardly.

Referring now to FIGS. 8A and 8B, after forming a subcutaneous pocket dimensioned to accept SID base 200, the surgeon can attach upper assembly 810 using a securing means 815 inserted through horizontal member 820 and into threaded aperture 745. Upper assembly 810 comprises horizontal member 820 having annular ring 830 disposed on a distal end thereof.

Cylindrical member 840 is slidingly disposed through annular ring 830. A circular handle 850 is disposed on an upper end of cylindrical member 840. A guide assembly 860 is disposed on the lower end of cylindrical member 840.

FIG. 8B shows a section view of surgical guide instrument 800 with platen 710 disposed within a subcutaneous pocket, as described hereinabove. Downward pressure can be applied to handle 850 to urge cylindrical member 840 downwardly through annular ring 830 such that blade assembly 860 passes through the skin and onto plastic disk 714 thereby forming a linear second incision through the skin.

The surgical guide instrument 800 is then removed from the patient. Implantation begins with skin attachment device 400 being inserted into the second incision made by the 860 guide such that tissues defining the periphery of that surgical incision are disposed within U-Shaped pocket 416 (FIGS. 4A, 4C). Skin attachment device 400 is then sutured to those tissues using the sets of apertures 440, 450, 460, 470, 480, and 490.

FIG. 6B illustrates a top view of skin attachment device 400 sutured to the periphery of an incision using sutures 620 through apertures 440, sutures 630 through apertures 450, sutures 640 through apertures 460, sutures 650 through apertures 470, sutures 660 through apertures 480, and sutures 670 through apertures 490. FIG. 6B further illustrates distal portion 230 and aperture 220 of cylindrical assembly 210 extending outwardly through aperture 430 in skin attachment device 400.

SID base 200 is then moved through the first incision into the subcutaneous pocket formed using the platen base 710, and the distal end 230 of cylindrical assembly 210 is inserted in and through aperture 430 of the skin attachment device 400 which has already been sutured to the patient.

Fixturing assembly 500 is then disposed around a distal portion of cylindrical assembly 210 that extends outwardly from skin attachment device 400. Fixturing assembly 500 is then attached to skin attachment device 400.

FIG. 6C illustrates fixturing device 500 disposed on lip 412 of skin attachment device. FIG. 6C further illustrates fastening devices 680 and 685 extending through apertures 420 and 425, respectively, to attach fixturing assembly 500 to skin attachment device 400. In addition, FIG. 6C further illustrates fastening device 690 extending though lateral aperture 540A and into threaded aperture 550B to attach sub-assembly 501A to sub-assembly 501B to form fixturing assembly 500.

Finally, SID cap 300 is attached to distal end 230 of cylindrical assembly 210.

Figure 9:
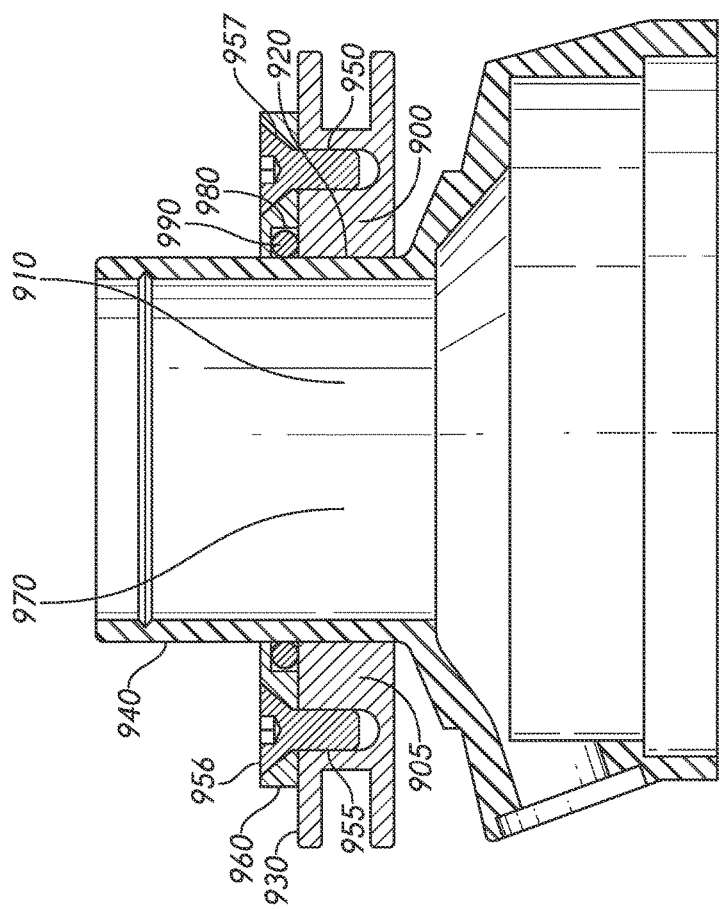
FIG. 9 is across section view illustrating Applicants' skin interface device ("SID")
Figure 10:
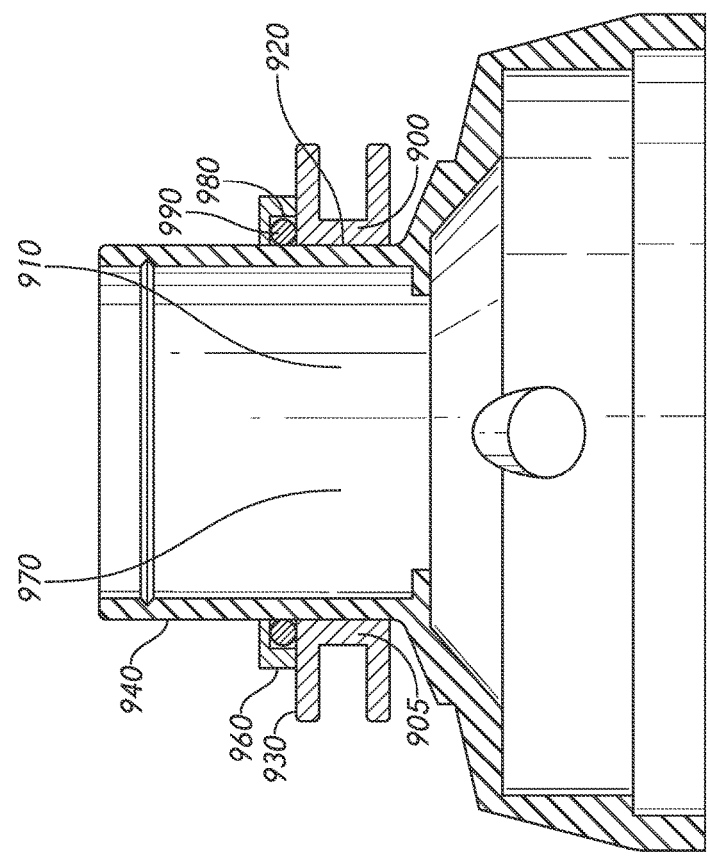
FIG. 10 is a cross section view illustrating Applicants' skin interface device ("SID").

Referring to FIGS. 9 and 10, skin attachment device 900 is formed to include a circular aperture 910 extending therethrough. Aperture 910 is defined by cylindrical wall 920. As described hereinabove, during implantation a distal portion of cylindrical assembly 940 will be passed through aperture 910 such that cylindrical wall 920 is in contact with cylindrical assembly 940.

Skin attachment device 900 is further formed to include one or more sets of apertures 440, 450, 460, 470, 480, and 490 (as shown in FIG. 4) extending through lip 930. During implantation, the tissues defining the periphery of a surgical incision described immediately hereinabove will be sutured to skin attachment device 900 using these apertures.

Skin attachment device 900 is further formed to optionally include a set of threaded apertures 950 and 955 extending into lip 930. During implantation, fixturing assembly 960 will be placed in contact with lip 930, such that a set of apertures 530 (FIG. 5A) and 540 (FIG. 5A) extending through fixturing device 960 overlie threaded apertures 950 and 955, respectively. Fastening devices can then to used to attach fixturing assembly 960 to skin attachment device 900.

Fixturing assembly 960 comprises an elliptical shape and is formed to include a circular aperture 970 extending therethrough. Aperture 970 is defined by cylindrical wall 920. In embodiments, surface 920 includes an annular recesses 980 to house a gasket ring 990, such as a silicone gasket ring.

As in FIG. 5, fixturing assembly 960 of SID 900 may be formed to include vertical apertures 956 and 957 extending therethrough. As described hereinabove, during implantation fixturing assembly 960 will be placed in contact with tissue attachment device 905, such that vertical apertures 956 and 957 overlie threaded aperture 955 and 950, respectively. Fastening devices can then be passed through vertical apertures 956 and 957 and into threaded apertures 955 and 950, respectively, to attach fixturing assembly 960 to skin attachment device 900.

Finally, one or more surfaces of the SID of the present invention, for example any surface the contacts skin, is texturized to promote adherence to the skin, for example by vapor blasting.

While the preferred embodiments of the present invention have been illustrated in detail, it should be apparent that modifications and adaptations to those embodiments may occur to one skilled in the art without departing from the scope of the present invention as set forth herein.

I claim:

1. A skin attachment device, comprising:
   a) an annular ring having a central aperture extending therethrough and defining an inside surface;
   b) a fixturing assembly,
      wherein the fixturing assembly is adapted to couple to the annular ring via one or more threaded screws which extend through apertures disposed in the fixture assembly and are received by one or more threaded apertures disposed in the annular ring,
      wherein the annular ring further comprises a groove extending annularly around an outside surface of the ring thereby defining upper and lower lips,
      wherein the upper lip comprises one or more vertical apertures extending therethrough adapted to accept a suture, and
      wherein the groove is texturized to promote tissue ingrowth upon implantation of the skin attachment device.

2. The skin attachment device of claim 1, wherein the fixturing assembly comprises a central aperture extending therethough thereby defining an inner surface.

3. The skin attachment device of claim 2, wherein the central aperture of the fixturing assembly is circular.

4. The skin attachment device of claim 3, wherein the fixturing assembly comprises one or more portions.

5. The skin attachment device of claim 4, wherein the fixturing assembly comprises 2 portions.

6. The skin attachment device of claim 2, wherein the inner surface of the fixturing assembly comprises an annular groove.

7. The skin attachment device of claim 6, wherein a gasket is disposed within the annular groove.

8. The skin attachment device of claim 7, wherein the gasket is silicon.

9. The skin attachment device of claim 1, wherein the groove is texturized via vapor blasting.

10. The skin attachment device of claim 1, wherein the groove is coated with one or more agents that promote tissue ingrowth.

11. The skin attachment device of claim 1, wherein the device is composed of titanium.

12. The skin attachment device of claim 1, wherein the device comprises 2, 3, 4, 5, 6, 7, 8, 9, or more sets of vertical apertures.

13. A method of performing a medical procedure comprising implanting the skin attachment device of claim 1.

14. A skin interface device (SID), comprising
a SID cap comprising a first housing, an annular sleeve, and a first annular winding disposed over said annular sleeve; and
a SID base comprising a second housing formed to include a tubular portion, a cylindrical member disposed in said tubular portion, and a second annular winding disposed around said cylindrical member, and further comprising the skin attachment device of claim 1;
wherein:
said SID cap is configured to be rotationally attached to said SID base;
when said SID cap is attached to said SID base, said second annular winding is disposed within said first annular winding;
when said SID cap is attached to said SID base, the relative positions of said first annular winding and said second annular winding are fixed both laterally and vertically.

15. The skin interface device of claim 14, wherein said annular sleeve comprises a ceramic material.

16. The skin interface device of claim 15, wherein said ceramic material comprises nickel, zinc, and/or manganese moieties.

17. The skin interface device of claim 14, wherein:
said SID base comprises a portion configured to be subcutaneously implanted into a subject;
said subcutaneous implant portion comprises a fabric cover formed to include a plurality of pores extending therethrough; and
said plurality of pores are formed to include diameters sufficient to allow cells to form attachments thereto.

18. The skin interface device of claim 14, further comprising:
a processor, wherein said processor is in electrical communication with said second winding;
a non-transitory computer readable medium, wherein said processor is in communication with said non-transitory computer readable medium;
computer readable program code encoded in said non-transitory computer readable medium; and
data encoded in said non-transitory computer readable medium.

19. The skin interface device of claim 18, wherein the data comprises information regarding the operational status of the device.

20. The skin interface device of claim 19, wherein:
said data comprises timing data;
when a patient having an implanted cardiac assist device changes a pump drive unit, a new pump drive unit reads said timing data from said non-transitory computer readable medium.

21. The skin interface device of claim 19, wherein the data pertains to an error in operation of a component, timing or volume of fluid pumping, pumping pressure, or usage of a component.

22. The skin interface device of claim 18, wherein the data comprises information of status of the patient.

23. The skin interface device of claim 22, wherein data comprises patient medical history or a physiological parameter.

24. The skin interface device of claim 23, wherein the physiological parameter is selected from EKG signals, pulse, body temperature, blood pressure, a blood analyte concentration, or a combination thereof.

25. The skin interface device of claim 18, wherein the data comprises an event log or status log.

26. The skin interface device of claim 18, wherein data is collected and stored as a function of time.

27. The skin interface device of claim 18, wherein said non-transitory computer readable medium comprises a rewritable memory device.

28. The skin interface device of claim 18, wherein said non-transitory computer readable medium comprises a non-volatile memory device.

29. The skin interface device of claim 18, further comprising:
a first infrared transceiver assembly disposed in said SID cap;
a second infrared transceiver assembly disposed in said SID base;
wherein:
said second infrared transceiver assembly is in electrical communication with said second winding; and
said second infrared transceiver assembly is interconnected with said processor;
said first infrared transceiver assembly and said second infrared transceiver assembly are configured to bidirectionally communicate with one another wirelessly.

30. The skin interface device of claim 29, further comprising:
a wireless communication module disposed in said SID cap and configured to wirelessly communicate with one or more computing devices external to said skin interface device;
wherein:
said wireless communication module is interconnected with said first infrared transceiver assembly;
said wireless communication module is in communication with said controller via said first infrared transceiver assembly and said second infrared transceiver assembly.

31. The skin interface device of claim 30, wherein one or more of said plurality of connecting members are configured to be attached to one or more leads from a pressure sensor disposed in an arterial interface device.

32. The skin interface device of claim 18, further comprising:

a plurality of connecting members extending outwardly from SID base;
wherein
each of said plurality of connecting members is in communication with said processor; and
one or more of said plurality of connecting members are configured to be attached to one or more implanted EKG sensors.

33. The skin interface device of claim 14, further comprising circuitry operable to prevent an electric shock applied externally to the device from rendering the device inoperable.

34. The skin interface device of claim 33, wherein the electric shock is generated by a defibrillator.

35. The skin interface device of claim 33, wherein the electric shock has a voltage of about 100, 200, 300, 400, 500, 600, 700, 800 or greater.

36. The skin interface device of claim 14, wherein the device is operable for use with air as a pumping medium.

37. A skin interface device (SID) for an implantable cardiac assist device, comprising a processor, a non-transitory computer readable medium, and computer readable program code encoded in said non-transitory computer readable medium, the computer readable program code comprising a series of computer readable program steps to effect receiving signals from one or more implanted EKG sensors, and further comprising the skin attachment device of claim 1.

38. The skin interface device of claim 37, said computer readable program code further comprising a series of computer readable program steps to effect:
evaluating signals received from one or more implanted EKG sensors with reference to certain nominal signal characteristics encoded in computer readable program code; and
rejecting signals received from one or more interconnected EKG sensors when those signals do not meet said nominal signal characteristics.

39. The skin interface device of claim 37, said computer readable program code further comprising a series of computer readable program steps to effect combining signals received from one or more implanted EKG sensors.

40. The skin interface device of claim 37, said computer readable program code further comprising a series of computer readable program steps to effect analyzing signals received from one or more implanted EKG sensors to detect a QRS complex.

41. The skin interface device of claim 37, further comprising data encoded in said non-transitory computer readable medium.

42. The skin interface device of claim 41, wherein the data comprises information regarding the operational status of the device.

43. The skin interface device of claim 42, wherein the data pertains to an error in operation of a component, timing or volume of fluid pumping, pumping pressure, or usage of a component.

44. The skin interface device of claim 41, wherein the data comprises information of status of the patient.

45. The skin interface device of claim 44, wherein data comprises patient medical history or a physiological parameter.

46. The skin interface device of claim 45, wherein the physiological parameter is selected from EKG signals, pulse, body temperature, blood pressure, a blood analyte concentration, or a combination thereof.

47. The skin interface device of claim 41, wherein the data comprises an event log or status log.

48. The skin interface device of claim 41, wherein data is collected and stored as a function of time.

49. The skin interface device of claim 37, further comprising circuitry operable to prevent an electric shock applied externally to the device from rendering the device inoperable.

50. The skin interface device of claim 49, wherein the electric shock is generated by a defibrillator.

51. The skin interface device of claim 50, wherein the electric shock has a voltage of about 100, 200, 300, 400, 500, 600, 700, 800 or greater.

52. The skin interface device of claim 37, wherein the device is operable for use with air as a pumping medium.

53. An arterial interface device for implantation into a subject, comprising:
a body formed to include two lumens extending therethrough;
wherein a first lumen formed in said body is configured to accept a pneumatic drive line interconnecting a partially implanted skin interface device and an implanted pump cardiac assist device, wherein the body comprises the skin attachment device of claim 1.

54. The arterial interface device of claim 53, further comprising:
a pressure sensor;
wherein a second lumen formed in said body is configured to house said pressure sensor.

55. The arterial interface device of claim 54, further comprising:
a plurality of sensor leads extending outwardly from said body:
wherein said plurality of sensor leads are configured to be attached to said partially implanted skin interface device.

56. The arterial interface device of claim 55, wherein said plurality of leads comprises:
a power lead;
a clock lead;
a ground lead;
and a data lead.

57. The arterial interface device of claim 53, wherein the device is operable for use with air as a pumping medium.

* * * * *